US00PP14399P39

(12) United States Plant Patent
Pieters

(10) Patent No.: US PP14,399 P3
(45) Date of Patent: Dec. 23, 2003

(54) CHRYSANTHEMUM PLANT NAMED 'GEDI TWO FIO'

(50) Latin Name: *Chrysanthemum morifolium*
Varietal Denomination: Gedi Two Fio

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 10/137,807

(22) Filed: May 1, 2002

(65) Prior Publication Data

US 2003/0208814 P1 Nov. 6, 2003

(51) Int. Cl.[7] ..... A01H 5/00
(52) U.S. Cl. ..... Plt./289

(58) Field of Search ..... Plt./289, 287

(56) References Cited

PUBLICATIONS

Brummitt, Horticultural Science Chrysanthemum once again, The Garden, 1997, pp. 662–663.*

* cited by examiner

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant cultivar is disclosed, characterized by a decorative-type inflorescence, consistent flowering response to short days, blooming consistently after 49 days of short day length, free branching habit, yellow ray florets, a very uniform round growth habit, and a large quantity of blooms per flowering branch.

1 Drawing Sheet

Latin name of the genus and species: The present invention relates to a new and distinct cultivar of Chrysanthemum plant, botanically known as *Chrysanthemum morifolium.*

Variety denomination: The new and distinct Chrysanthemum plant is hereinafter referred to by the cultivar name 'Gedi Two Fio.'

BACKGROUND OF THE INVENTION

The new cultivar is a product of hybridization of a female parent Chrysanthemum plant variety 'Gedi VL8' (U.S. Plant Pat. No. 11,344) and a male parent Chrysanthemum plant variety 'Gedi One Sor' (U.S. Plant Pat. No. 13,901). The new cultivar was discovered and selected by the inventor in September 1996.

Asexual reproduction of the new cultivar by apical tip cutting and meristem tissue culture was performed in Oxnard, Calif. and has shown that the unique features of this cultivar are stable and reproduced true to type on successive generations.

SUMMARY OF THE INVENTION

The cultivar 'Gedi Two Fio' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Gedi Two Fio'. These characteristics in combination distinguish 'Gedi Two Fio' as a new and distinct Chrysanthemum cultivar:

1. Decorative-type inflorescence,
2. Consistent flowering response to short days, blooming consistently after 49 days of short day length,
3. Free branching habit, 4. Yellow ray florets,
5. Very uniform round growth habit, and
6. Large quantity of blooms per flowering branch.

Plants of the new cultivar are similar to plants of the female parent variety, 'Gedi VL8' in most horticultural characteristics, however plants of the new cultivar have ray florets of a different color, more inflorescences per flowering branch, and a smaller diameter bloom than plants of the female parent variety.

Plants of the new cultivar are similar to plants of the male parent variety, 'Gedi One Sor' in most horticultural characteristics, however plants of the new cultivar have fewer ray florets, more blooms per flowering branch, and a smaller diameter bloom than plants of the male parent variety.

In comparison to the commercially available variety 'Cleargar GFI' (U.S. Plant Pat. No. 10,463), 'Gedi Two Fio' blooms earlier naturally, has fewer ray florets per inflorescence, and has more inflorescences per flowering branch.

BRIEF DESCRIPTION OF THE PHOTOGRAPH

The photograph shows a plant of 'Gedi Two Fio' grown in a six-inch container. One cutting was used in the pot.

DETAILED BOTANICAL DESCRIPTION

In the following description, color references are made to The Royal Horticultural Society Colour Chart except where general terms of ordinary dictionary significance are used. The following observations and measurements describe plants grown in Oxnard, Calif. during the month of December and January. The age of the observed plants is 94 days from a rooted cutting. The growing temperature ranged from 55° to 68° F. at night to 60° to 75° F. during the day.

Measurements and numerical values represent averages of typical flowering types.

Botanical classification: *Chrysanthemum morifolium* cultivar 'Gedi Two Fio'.
Commercial classification: Garden-type Chrysanthemum.
Parentage: Hybridization of a female parent Chrysanthemum plant variety, 'Gedi VL8' (U.S. Plant Pat. No. 11,344), and a male parent Chrysanthemum plant variety 'Gedi One Sor' (U.S. Plant Pat. No. 13,901).

PROPAGATION

Time to rooting: 7 to 14 days at approximately 21° C.
Root description: Fine, fibrous.

PLANT

Growth habit: Mounding herbaceous perennial.
Height: Approximately 24.5 cm.
Spread: Approximately 24 cm.
Growth rate: Moderate.
Branching characteristics: Free Branching.
Length of lateral branches: Approximately 23 cm.
Number of leaves per lateral branch: Approximately 13.

FOLIAGE

Leaf:
- *Arrangement.*—Alternate.
- *Average length.*—Approximately 4.8 cm.
- *Average width.*—Approximately 3.7 cm.
- *Shape of blade.*—Ovate.
- *Apex.*—Cuspidate.
- *Base.*—Attenuate.
- *Attachment.*—Stalked.
- *Margin.*—Palmately lobed.
- *Texture of top surface.*—Lightly pubescent.
- *Texture of bottom surface.*—Lightly pubescent.
- *Color.*—young foliage upper side: Near 137D. young foliage under side: Near 138A. mature foliage upper side: Near 137A. mature foliage under side: Near 138A. venation upper side: Near 138C. venation under side: Near 138B.
- *Venation type.*—Palmately net.

Petiole:
- *Average length.*—Approximately 2.2 cm.
- *Color.*—Near 137A.
- *Diameter.*—Approximately 0.2 cm.

BLOOM

Inflorescence:
- *Flowering habit.*—Induced by darkness period greater than 13.5 hours, approximately 49 days of appropriate day length required to induce and develop blooms.
- *Inflorescence form.*—Decorative.
- *Natural flowering season.*—Approximately the middle two weeks of September.
- *Number of inflorescences per lateral branch.*—Approximately 18.
- *Inflorescence diameter.*—Approximately 3.3 cm.
- *Inflorescence depth.*—Approximately 1.7 cm.
- *Inflorescence longevity on plant.*—Approximately 25 days.
- *Persistence.*—Persistent.

Ray florets:
- *Appearance.*—Matte.
- *Texture.*—Smooth.
- *Average number per flower.*—135.
- *Shape.*—Obovate.
- *Aspect.*—Flat.
- *Margin.*—Entire.
- *Apex.*—Retuse.
- *Length.*—Approximately 1.3 cm.
- *Width.*—Approximately 0.6 cm.
- *Color.*—Upper surface at first opening: Near 9A. Upper surface at maturity: Near 7A with near 15A at the center and around the margin. Upper surface at fading: Near 7A with near 20A at the center and around the margin. Under surface at first opening: Near 12B. Under surface at maturity: Near 7C with near 167D at the center and around the margin. Under surface at fading: Near 13C with near 167C at the center and around the margin.

Disc florets:
- *Appearance.*—Shiny.
- *Texture.*—Smooth.
- *Average number per flower.*—Approximately 25.
- *Shape.*—Cylindric.
- *Apex.*—Obtuse.
- *Average length.*—Approximately 0.5 cm.
- *Average width.*—Approximately 0.1 cm.
- *Color.*—At first opening: Near 15A. At maturity: Near 14B. At fading: Near 14A.

Peduncle:
- *Length.*—At terminal end (shortest): Approximately 2.8 cm. At lateral end (longest): Approximately 6.8 cm.
- *Angle to stem.*—Acute.
- *Strength.*—Moderate.
- *Color.*—Near 138A.
- *Habit.*—Upright.
- *Diameter.*—Approximately 0.2 cm.
- *Surface texture.*—Lightly pubescent.

Inflorescence bud:
- *Length.*—Approximately 0.4 cm.
- *Diameter.*—Approximately 0.7 cm.
- *Form.*—Globular.
- *Color.*—Near 144B.

Involucral bracts (phyllaries):
- *Appearance.*—Matte.
- *Texture.*—Lightly pubescent.
- *Number.*—Approximately 34.
- *Shape.*—Oblanceolate.
- *Margin.*—Entire.
- *Apex.*—Acute.
- *Length.*—Approximately 0.6 cm.
- *Width.*—Approximately 0.2 cm.
- *Color.*—Upper side: Near 143A. Under side: Near 143A.

REPRODUCTIVE ORGANS

Ray florets:
- *Number of pistils per flower.*—1.
- *Stigma shape.*—2 branched.
- *Stigma color.*—Near 5C.
- *Style color.*—Near 1C.
- *Style length.*—Approximately 0.3 cm.
- *Stamens.*—Absent.

Disc florets:
- *Number of pistils per flower.*—1.
- *Stigma shape.*—Two-branched.
- *Stigma color.*—Near 14B.
- *Style length.*—Approximately 0.3 cm.

*Style color.*—Near 154D.
*Number of stamens per flower.*—4.
*Anther shape.*—Tubular.
*Anther color.*—Near 13A.
*Pollen color.*—Near 13A.

OTHER CHARACTERISTICS

Seed production: Commercially, this plant is not used or observed in a stage wherein seeds would be produced. Therefore, seed production has not been observed.

Disease resistance: Neither resistance nor susceptibility to diseases and pests has been observed in this cultivar.

Heat and cold resistance: Plants with flowers are hardy to low temperatures about −2° C. Non flowering plants are hardy in the approximate range of 3° C. to −6° C., depending upon duration of cold and amount of moisture in the soil. With adequate water plants are hardy to a high temperature of 49° C.

What is claimed is:

1. A new and distinct cultivar of Chrysanthemum plant named 'Gedi Two Fio' as herein illustrated and described.

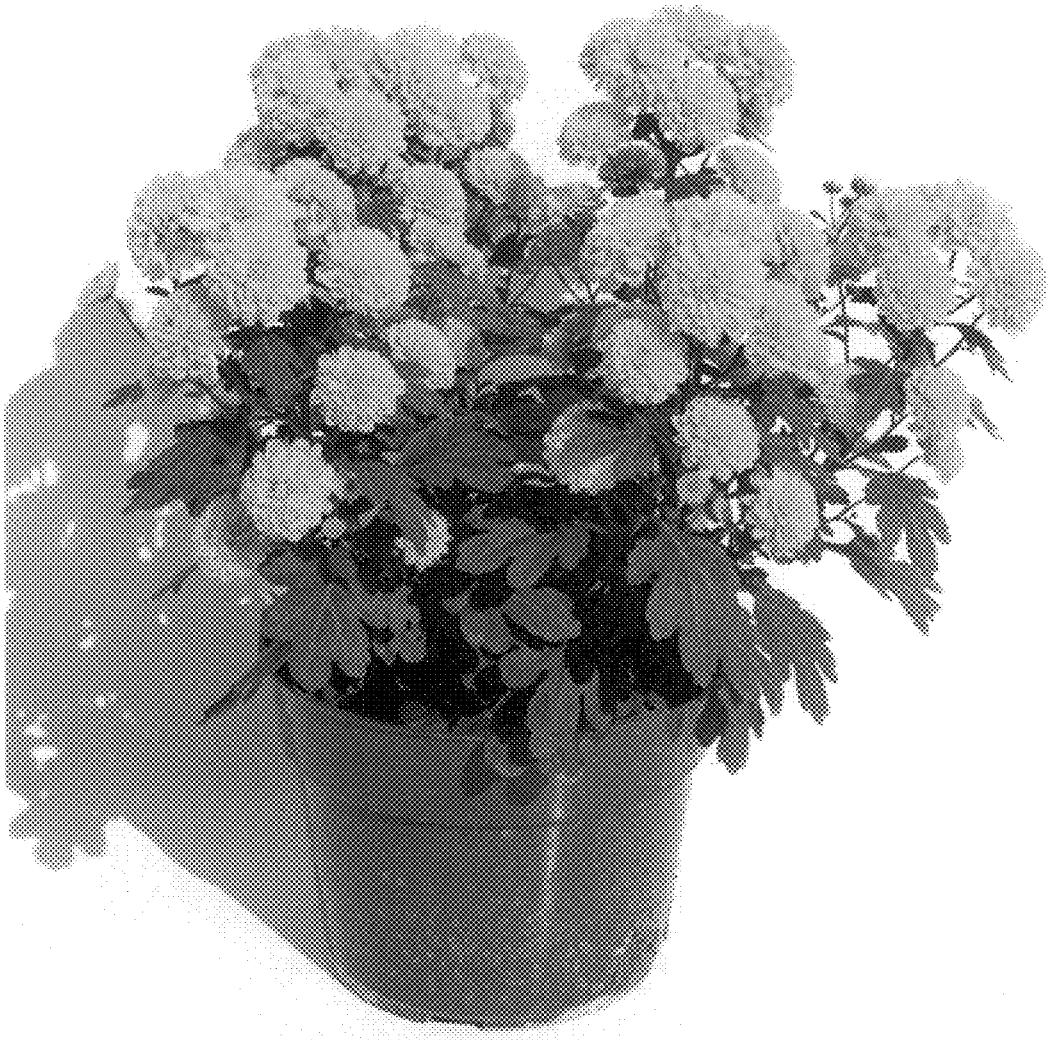

* * * * *